United States Patent
Carman et al.

(10) Patent No.: US 6,337,048 B1
(45) Date of Patent: *Jan. 8, 2002

(54) SOLUBILITY AND DISPERSIBILITY BY EXPOSURE TO $O_X$

(75) Inventors: Gary B. Carman, Reno; Stephen K. Wirtz, Sparks, both of NV (US)

(73) Assignee: Cosmed Group, Inc., Coventry, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/532,649

(22) Filed: Mar. 22, 2000

Related U.S. Application Data

(63) Continuation-in-part of application No. 09/217,581, filed on Dec. 22, 1998.
(60) Provisional application No. 60/068,668, filed on Dec. 23, 1997.

(51) Int. Cl.$^7$ .................................................. A01N 1/00
(52) U.S. Cl. ............................ 422/33; 422/22; 422/23; 422/28; 422/33; 422/186.07; 422/292; 422/300; 422/305
(58) Field of Search ............................ 422/22, 23, 28, 422/33, 186.07, 292, 300, 305; 426/590

(56) References Cited

U.S. PATENT DOCUMENTS

| | | | |
|---|---|---|---|
| 4,182,663 A | | 1/1980 | Vaseen ........................ 204/157 |
| 4,640,782 A | * | 2/1987 | Burleson ....................... 422/22 |
| 5,085,883 A | * | 2/1992 | Garleb et al. ................. 426/590 |
| 5,104,676 A | * | 4/1992 | Mahmoud et al. ........... 426/590 |
| 5,135,721 A | | 8/1992 | Richard ....................... 422/111 |
| 5,178,896 A | | 1/1993 | Langner ...................... 426/590 |
| 5,200,158 A | | 4/1993 | Jacob .......................... 422/292 |
| 5,413,758 A | * | 5/1995 | Caputo et al. ................. 422/22 |

* cited by examiner

Primary Examiner—Robert J. Warden, Sr.
Assistant Examiner—Imad Soubra
(74) Attorney, Agent, or Firm—Piper Marbury Rudnick & Wolfe LLP; Laura A. Donnelly

(57) ABSTRACT

A method and apparatus for significantly increasing the solubility and dispersibility of consumer products such as food products, botanicals, cosmetic ingredients and medical products is disclosed. The method involves applying a continuous stream of oxygen-containing, i.e., $O_X$ gas to a material in a sealed chamber. The continuous stream of $O_X$ gas is prepared in an $O_X$ generation cell, which contains a means for generating the $O_X$ gas at a pressure less than 20 lbs/in$^2$ using, for example, one or more of the following: corona discharge, high frequency electrical discharge, ultraviolet light, x-ray, radioactive isotope and electric beam. The apparatus contains:

(a) a chamber;

(b) a vacuum pump coupled to the chamber;

(c) an $O_X$ generation cell, wherein the $O_X$ generation cell contains an $O_X$ generator capable of generating $O_X$ at a pressure less than 20 lbs/in$^2$.

(d) a first control valve coupled to the chamber and the $O_X$ generation cell, wherein the first control valve is capable of permitting $O_X$ to be drawn from the $O_X$ generation cell into the chamber; and (e) a second control valve coupled to the chamber, wherein the second control valve is capable of withdrawing $O_X$ contained within the chamber.

21 Claims, 3 Drawing Sheets

SOLUBILITY AND DISPERSIBILITY BY EXPOSURE TO $O_x$

This application is a continuation-in-part of U.S. application Ser. No. 09/217,581 filed Dec. 22, 1998, which is a regular National application claiming priority from Provisional Application, U.S. application Ser. No. 60/068,668, filed Dec. 23, 1997. The entirety of both are incorporated herein by reference.

BACKGROUND OF THE INVENTION

Field of the Invention

The present invention generally relates to a method and apparatus that can be utilized to significantly increase the solubility and dispersibility of consumer products such as food products, botanicals, cosmetic ingredients and medical products while at the same time reducing the biological load on such products. The products include those that have traditionally been treated with commercial sterilants or fumigants such as ethylene oxide, propylene oxide, methyl bromide, hydrogen phosphide, steam (heat), irradiation, and the like.

Currently, ethylene oxide (EO) is the agent of choice for virtually all of the gaseous sterilization of consumer products performed in the United States. However, as discussed in U.S. application Ser. No. 09/217,581, EO has a number of properties which limit its use as a sterilant.

Over the last fifty years, a number of other gases that lack one or more of the disadvantages of EO have been tested as sterilants. These gases include, for example, hydrogen peroxide, ozone and chlorine dioxide. However, as disclosed in U.S. application Ser. No. 09/217,581, prior to the invention disclosed therein, no other gas has proven to be as efficacious as EO for use in large volume industrial sterilizers.

A number of commercial fumigants are presently used to treat foodstuffs and other stored commodities. The most widely used fumigants are methyl bromide, hydrogen phosphide, carbon dioxide, and hydrogen cyanide. As disclosed in U.S. application Ser. No. 09/217,581, many of these compounds pose hazardous conditions for application personnel and can form deleterious residues in the foodstuffs and commodities that are treated. Furthermore, some of the above-mentioned traditional sterilants and fumigants have been identified with the formation of carcinogens and mutagens, thus limiting the products that can be treated.

Other procedures that have been developed to treat products utilize heat, ionizing radiation, and other chemical compounds. All of these procedures are potentially detrimental to the products' nutritional, physical and/or chemical attributes and thus make them undesirable.

U.S. application Ser. No. 09/217,581 discloses a method and apparatus to reduce biological loads in consumer products to eliminate human pathogens while maintaining product stability. The present inventors have surprisingly discovered that the method and apparatus disclosed in U.S. application Ser. No. 09/217,581 can also be used to increase the solubility and dispersibility of consumer products.

Although not limited to the following, the present invention in particular relates to method and apparatus that can be utilized to increase the solubility and improve the dispersibility of materials that are not naturally soluble in water (e.g., psyllium fiber) Ming $O_x$. Thus, the present invention also relates to a highly soluble psyllium that has improved solubility and dispersibility in liquids.

Products containing psyllium seed husk (hereinafter also referred to as "psylliumn") are known to be useful for the benefit of normalizing bowel function and Taxation. In addition, recent research has demonstrated the effectiveness of psyllium seed fiber in reducing human serum cholesterol levels and in controlling blood glucose levels in diabetics.

Psyllium seed husk contains natural mucilage. It forms a gelatinous mass on contact with water, and it exhibits poor dispersibility and mixability in water. The psyllium husk particles tend to agglomerate when mixed with water. Hydration takes place over the surface of such agglomerated aggregates to form gel-coated lumps, the interiors of which are still substantially dry. These lumps are extremely difficult to disperse.

One way of reducing these problems while improving the taste of the psyllium product has been to use high percentages of sugar in the drink mix. The dispersibility and mixability are improved, but diabetics and people on reduced calorie diets may have difficulty taking such products in view of the high sugar content.

U.S. Pat. No. 4,321,263 to Powell et al. discloses a method of improving the dispersibility of psyllium powder. It is described therein to wet the psyllium particles with an alcoholic solution of at least one of polyethylene glycol and polyvinylpyrrolidone and granulating the thus-coated particles.

U.S. Pat. Nos. 4,459,280 and 4,548,806 to Colliopoulos et al. describe improving mixability and dispersibility of psyllium mucilloid by applying a film of hydrolyzed starch oligosaccharide, a mono- or di-saccharide, a polyglucose, or a polymaltose to the psyllium. Preferred therein is agglomerating the psyllium mucilloid.

U.S. Pat. No. 4,551,331 to Rudin describes a modified dry dietary fiber product which is said to be readily dispersible in liquids. The dry dietary fiber product (e.g., psyllium) comprises a coating of from 0.05 to 20% of a food grade emulsifier. The processes for making such products are said to comprise blending the dietary fiber product materials with the mixture of a non-toxic solvent in a food grade emulsifier follow by removing the solvent.

U.S. Pat. No. 4,828,842 to Furst et al. discloses a fibrous, vegetable material coated with a combination of a major amount of hydroxypropyl methylcellulose and a minor amount of polyethylene glycol to aid in the wetting and dispersing of the fibrous, vegetable material.

U.S. Pat. No. 5,219,570 to Barbera discloses the use of an edible acid dispersed throughout the agglomerating coating applied to psyllium husk to improve mixability, dispersibility, and product aesthetics, for psyllium husk products having low (less than about 20%) sugar content.

Each of the methods described above require treating the psyllium product with one or more substances to increase the solubility and dispersibility thereto. Thus, while there has already been much research devoted to improving the solubility and dispersibility of products such as psyllium in liquids, there continues to be a need for improved products and processes for obtaining readily soluble, dispersible products.

It is therefore an object of the present invention to provide commercial products having improved solubility and dispersibility in a liquid such as water.

SUMMARY OF THE INVENTION

The method and apparatus of the present invention increase the solubility and dispersibility of consumer products during sterilization or fumigation, even while the product is in its original container (e.g., burlap bag, fiber drum, kraft paper bag, plastic bag, etc.).

The method of the present invention utilizes a gaseous mixture containing $O_1$, $O_2$ and $O_3$ (hereinafter referred to as "$O_X$") in a technologically advanced treatment system. Prior $O_3$ treatments of consumer products include, for example, (1) the submersion of an article in ozone-containing watered the bubbling of ozonated water over article (see, e.g., U.S. Pat. No. 4,517,159 to Karlson, and U.S. Pat. No. 4,640,872 to Burleson); and (2) the static treatment of medical devices and food products with gaseous ozone (see, e.g., U.S. Pat. No. 3,179,017 to Shapiro et al., U.S. Pat. No. 5,069,880 to Karlson, and U.S. Pat. No. 5,120,512 to Masuda.) Systems utilizing ozone as described above have encountered several limitations. The incorporation of ozone gas into water and then submersion of item(s) or the spraying of ozone treated water onto the surface of item(s) limits the process to products that can be soaked in water. The few gaseous uses of ozone have been limited to the surface treatment of medical devices and the like due to the lack of adequate penetration into compacted products. Thus, although these past processes have proven the efficacy of ozone as a sterilant, the limitation of the use of ozone as a surface treatment has not presented ozone as a reliable sterilant or fumigant for products contained within commercial containers. Furthermore, until recently, high concentration ozone generators, which would have allowed the present invention to properly function, have not been commercially available.

The present invention requires a relatively high concentration of $O_X$ for an extended treatment period to assist the required permeation of the $O_X$ into the substrate being treated. In addition to the generation of the ozone molecule, the present invention also utilizes the quenching effect of other inert gases to assist ozone generation, thereby increasing the stability of the $O_X$ radicals. A combination of oxygen, carbon dioxide, argon, and nitrogen have been used in the method of the present invention to achieve these factors. In addition to the benefits discussed above, the use of small quantities of carbon dioxide results in an increase in the rate of respiration in insects and some microbes, thus further aiding the action of the $O_X$ gases. Furthermore, the presence of atmospheric nitrogen has been utilized in the food industry for many years to protect sensitive oils and fats from oxidative rancidity. Small quantities of nitrogen can be used in the method of the present invention to assist in the protection of sensitive food components as well as assisting in the stabilization of the $O_X$ generation.

As an aid to understanding the invention, but without being limited thereby, the present invention is based on the discovery of the following:

1. That the method of the invention significantly reduces the hydrophobic characteristics of such products, as demonstrated below using psyllium husk, by fractionating the surface waxes or oils without damaging the gums or the cellular structure of the product. This is an advantage over other processes which may utilize chemical solvents or milling techniques.

2. That thermal degradation does not occur, since the method operates at temperatures near or below normal ambient temperatures. Superheated steam systems tend to cause some damage to these products by driving off desirable volatile compounds, color shifts, and incorporating undesirable moisture in or on the product.

3. That a slight surface bleaching is evident upon treating products such as psyllium. This is a desirable trait as the product is utilized in the industry. Typically, brown, yellow and red products demonstrate a greater degree of bleaching than do green products. whereas the $O_X$ treated psyllium remained suspended for a minimum of 24 hours.

4. That residues were not created during the inventive method. Although normal oxidation reactions occurred, the $O_X$ radicals rapidly reverted to atmospheric oxygen.

5. Powder agglomeration and extrusion techniques have previously been utilized to assist the mixing of powdered products into aqueous and other solutions. Unfortunately, the agglomeration process also incorporates and encapsulates microbiological organisms which protects the organisms from traditional fumigation and sterilization agents. The method of the invention initially reduces the microbiological load and leaves the product available to be treated by other fumigants and sterilants if further bio-reduction is desired.

Accordingly, it is an object of the present invention to provide a method and apparatus for increasing the solubility and dispersibility of consumer products.

It is another object of the present invention to provide a method and apparatus for increasing the solubility and dispersibility of consumer products in a safe manner.

It is a further object of the present invention to provide a simple, efficient and economical method and apparatus for increasing the solubility and dispersibility of consumer products that can be used at the site of production and/or packaging of such products.

In accordance with the above and other objects, the inventive method comprises applying a continuous stream of $O_X$ gas to a material in a sealed chamber. The continuous stream of $O_X$ gas is prepared in an $O_X$ generation cell, which contains a means for generating the $O_X$ gas at a pressure less than about 20 lbs./in$^2$ using, for example, one or more of the following: corona discharge, high frequency electrical discharge, ultraviolet light, x-ray, radioactive isotope and electron beam.

As discussed herein, a small percentage of $N_2$, $CO_2$ and/or Ar may be added during $O_X$ treatment. The addition of 0% to 15% $N_2$, 1% to 80% $CO_2$ and/or 1% to 18% Ar increases the generation of an $O_X$ quenching effect. Penetration of $O_X$ into the material being treated is thus enhanced. In addition, Argon is unique among the (inert) Noble Gases, in that is soluble in both water and organic liquids. (The Merck Index Eleventh Edition.) This characteristic theoretically enables Argon to become a glue of sorts. Argon is capable of attaching to gases without reacting thereto. Argon thus assists in $O_X$ quenching by attaching to the $O_X$ molecules and preventing the $O_X$ molecules from colliding into each other. Argon also loosely binds hydrophilic and hydrophobic materials, thus allowing one to be diffused through the other, with reacting with either. This characteristic is useful in accelerating the diffusion of $O_X$ into and through hydrophobic materials such as fats, oils and cell walls.

The inventive apparatus comprises:

(a) a chamber;

(b) a vacuum pump coupled to the chamber;

(c) an $O_X$ generation cell, wherein the $O_X$ generation cell contains a means for generating $O_X$ at a pressure less than about 20 lbs./in$^2$ using, for example, one or more of the following: corona discharge, high frequency electrical discharge, ultraviolet light, x-ray, radioactive isotope and electron beam;

(d) a first control valve coupled to the chamber and the $O_X$ generation cell, wherein the first control valve is capable of permitting $O_X$ to be drawn from the $O_X$ generation cell into the chamber; and (e) a second control valve coupled to the chamber, wherein the second control valve is capable of withdrawing $O_X$ contained within the chamber out of the chamber.

Water vapor may be introduced to the gaseous $O_X$ to maintain an appropriate humidity level, i.e., between about 20% and about 98% relative humidity, and, more preferably between about 40% and about 75% relative humidity. The appropriate humidity level is dependent upon the ambient humidity and upon the product being treated. For example, granular and powered products require a relatively low humidity level to prevent growth of mold and yeast thereon. However, depending on the length of treatment time, the vacuum created during the process removes humidity, thus requiring the addition of humidity. The $O_X$ gas may then be passed through a commercially available catalytic destruct unit to eliminate any residual $O_3$ and $O_1$ before the gas stream is discharged to the atmosphere.

The present invention is also directed to treated consumer products that result from use of the present inventive method and apparatus.

Additional objects and attendant advantages of the present invention will be set forth in the description and examples that follow, or may be learned from practicing the method or using the apparatus of the present invention. These and other objects and advantages may be realized and attained by means of the features, instrumentalities and/or combinations particularly described herein. It is also to be understood that the foregoing general description and the following detailed description are only exemplary and explanatory and are not to be viewed as limiting or restricting the invention as claimed.

The invention itself, together with further objects and attendant advantages, will best be understood by reference to the following detailed description, taken in conjunction with the accompanying drawings.

DESCRIPTION OF PREFERRED EMBODIMENTS

Figure 1:
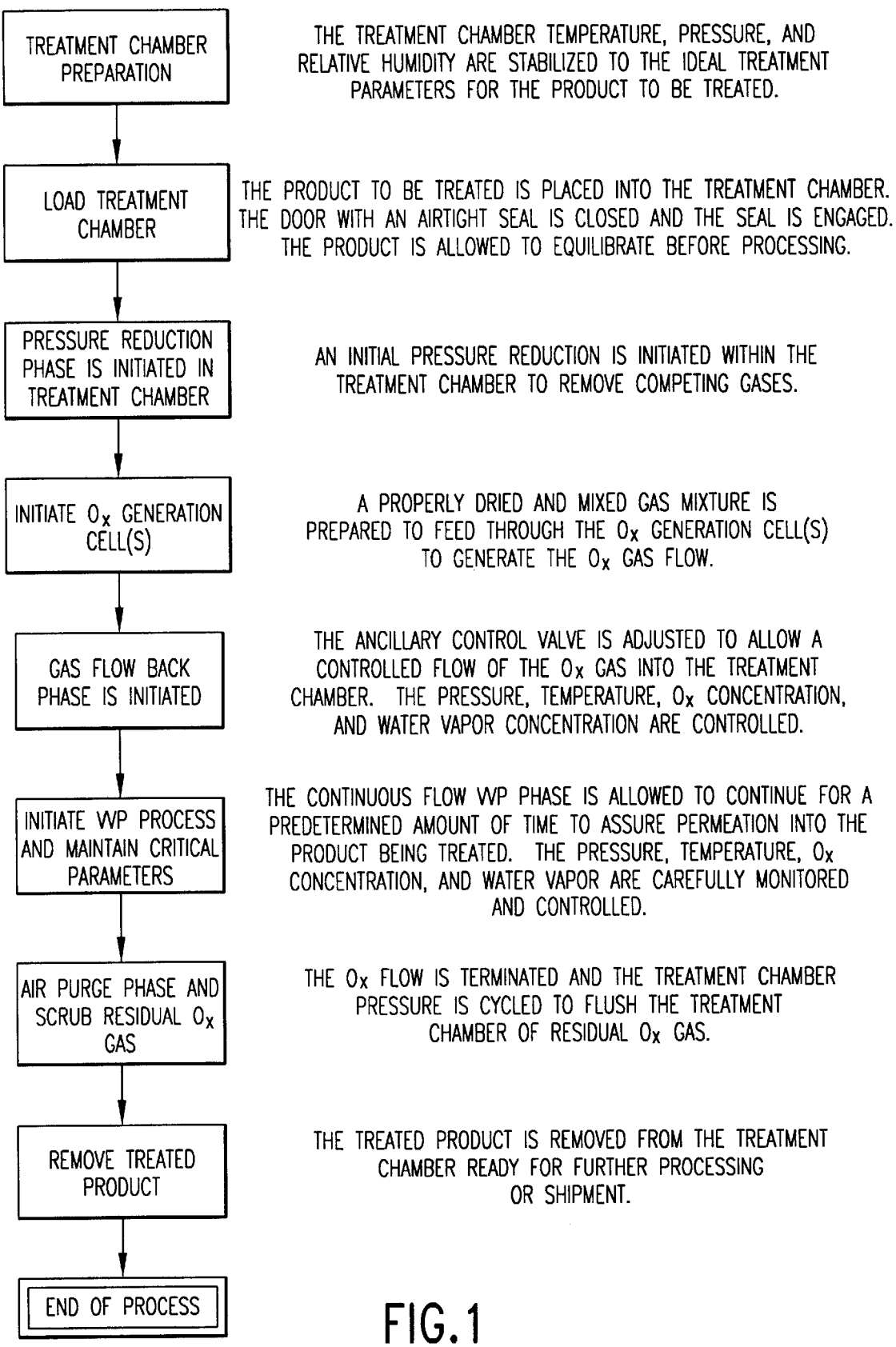
FIG. 1 is a flow chart showing an embodiment of a method for using a continuous flow of $O_X$ to increase solubility and dispersibility in accordance with the method of the present invention.

All patents, patent applications and literatures that may be cited herein are incorporated herein by reference.

Traditionally, botanical products such as psyllium husk have demonstrated hydrophobic characteristics due to natural waxes and oils on the surface of the seed coat, leaf, husk, etc. It is often desirable to increase the solubility, or "wetability", of these products to enhance rapid inclusion into a food or beverage with minimum agitation and the avoidance of clumps that resist dissolution. In the case of psyllium husk, which is extensively used as a laxative agent in the United States, Europe, and Asia, it is very desirable to promote a rapid mixing and even dissolution as to allow the consumer to ingest the psyllium beverage before the gum and soluble fiber content swell. Upon swelling, the psyllium beverage becomes unpalatable and, in some cases, potentially dangerous to individuals who may have swallowing impairments.

The method of the invention may be applied to grain (such as psyllium husk) and botanical materials in their raw state or after milling to provide the stated benefits. In addition to the stated functional benefit, the product microbiological and insect load is reduced or eliminated.

Previous uses of $O_3$ include the reliance upon filling a sterilization chamber with $O_3$ and exposing the materials to be treated in static fashion for various periods of time without replenishment of $O_3$. See for example, U.S. Pat. Nos. 3,719,017 and 5,069,880. Under these conditions, the concentration of $O_3$ within the chamber would be expected to rapidly decrease to a level below that required for effective biological burden reduction due to the short half life of $O_3$, which typically less than 20 minutes. A further disadvantage of the static exposure technology is the reliance on simple diffusion to promote permeation of the $O_3$ molecules through packaging materials and into voids and interstices of the materials being treated. Thus, such methods do not achieve adequate permeation of into the material being treated.

The present invention offers significant advances over prior technology in that it provides a uniformly high concentration of $O_X$, i.e., between about 3% and about 16%, throughout the treatment cycle and promotes rapid permeation of $O_X$ through packaging materials and into the voids and interstices of the materials undergoing treatment. Continuous operation of the vacuum pump and $O_X$ generator during treatment ensures that the concentration of $O_X$ remains high throughout the process by constantly supplying newly generated $O_X$ molecules to replace those molecules which have spontaneously degraded to inactive $O_2$ and those have reacted during the process. Operation of the vacuum pump during the process, as practiced in the present invention, also maintains a continuous pressure differential, which actively draws $O_X$ molecules through packaging materials and into the materials being treated.

Because $O_X$ is not flammable or explosive, facilities need not include damage-limiting construction or explosion-proof equipment. Moreover, $O_3$ is classified by the U.S. Food and Drug Administration as a generally recognized as safe "GRAS" substance.

Figure 3:
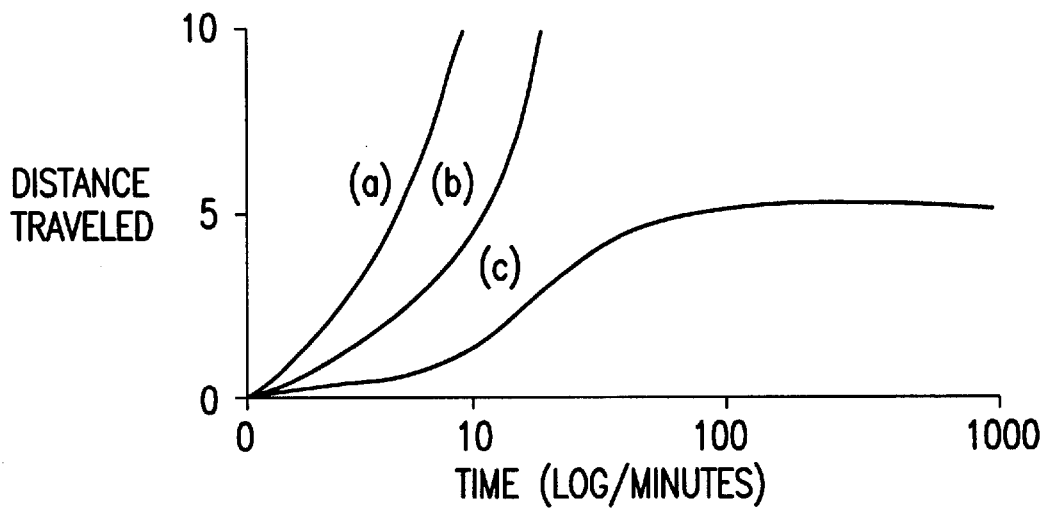
FIG. 3 is a graph comparing permeation of $O_X$ gas for (a) VVP+$CO_2$+$O_X$ in accordance with the method of the invention, (b) VVP+$O_X$ in accordance with the method of the invention, and (c) static+$O_X$ in accordance with conventional use of gaseous $O_X$ in a static fashion.

FIG. 3 is a graph comparing permeation of $O_X$ gas for (a) VVP+$CO_2$+$O_X$ in accordance with the method of the invention, (b) VVP+$O_X$ in accordance with the method of the invention and (c) static+$O_X$ in accordance with conventional use of gaseous $O_X$ in a static fashion. The static flow of gas (c) demonstrated a limited permeation, which quickly stopped altogether. The (VVP) process (a) and (b), on the other hand, demonstrated a continuous progression through the packed column; completely depleting the chemical indicator. The method of the present invention enhances the permeability of $O_X$ gases into commercially sized containers of granular and powdered food components. Via comparative data (see FIG. 3), a static flow of $O_X$ bearing gas (curve (c)) has shown ineffective in driving the $O_X$ into the containers. The method of the present invention utilizes a process herein described as the Vacuum Vapor Phase Dynamic Flow (VVP). In theory, and supported by empirical evidence, VVP acts as the driving force to enhance permeation of the $O_X$ gases by two factors. The first factor is the molecular acceleration of the $O_X$ gases due to the flashing of the concentrated $O_X$ gas into the reduced pressure treatment chamber. This creates a driving force at a molecular level that continuously forces the $O_X$ gases into the product being treated. The second factor is the resulting reduction of molecules within the reduced pressure treatment chamber which reduces the incidence of molecular collision of the $O_X$ gases. Molecular collision of the $O_X$ gases causes rapid degradation of the $O_3$ and $O_1$, radicals present therein, thereby reducing the gases' effectiveness. Without the VVP process, the $O_X$ gas flow could only be utilized as a surface treatment of non-amorphous materials. Therefore, the VVP process expands the capabilities of the present invention to process virtually any type of product in-situ, thus eliminating the need to repackage the product after treatment.

The method of the present invention avoids many of the limitations of previous uses of ozone by avoiding the need for water sprays and/or water immersion of the substance to be treated. Many products such as spices, flour-based products, sugar-based products, cosmetic bases, herbs, and botanicals, which are sensitive to high levels of moisture, can be treated using the method of the present invention. The method of the present invention also avoids the need to open conventional commercial packaging before treatment, thus avoiding unnecessary product degradation and loss. The product is treated in situ utilizing a conventional metal chamber with the product palletized in its normal shipping configuration. Previous methods have required the product to be agitated, blended, bubbled, or re-packaged during or immediately upon completion of treatment. Due to the increased permeation of the $O_X$ gas mixture, these damaging handling practices are avoided. The unique gas mixture also assists in the stabilization of the $O_X$ generation through its quenching effect. The extended half life of the $O_X$ radicals allows the active portions of the treatment gas to fully penetrate the substrate and act upon offending organisms. In combination with carbon dioxide, the stabilized $O_X$ gas mixture is further enhanced by the increased respiration rates of the offending organism(s) while in the presence of the permeated $O_X$ gases. The method of the present invention protects such products by processing them under relatively cool conditions, i.e., between about 32° F. and about 80° F.

Figure 2:
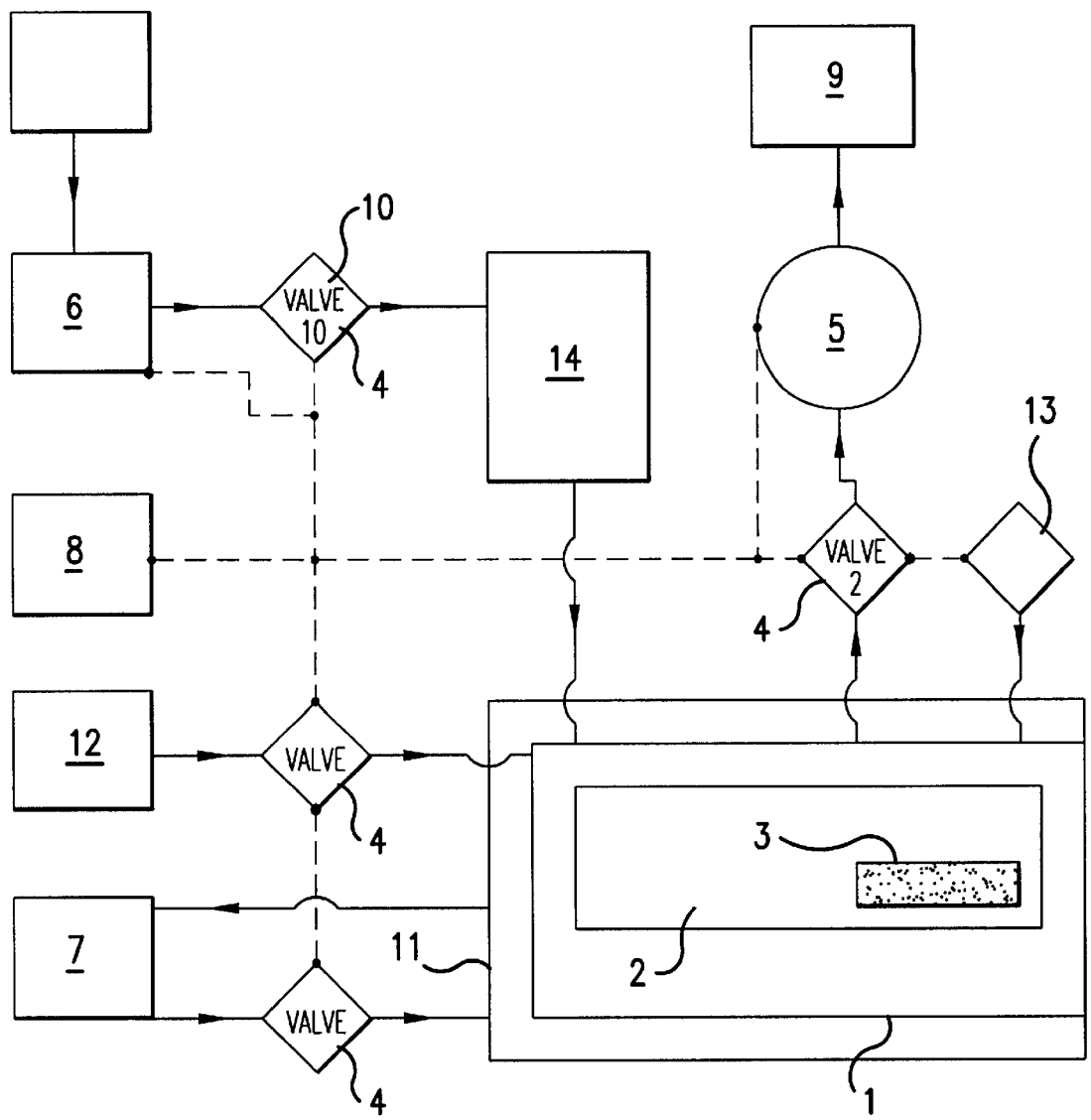
FIG. 2 is a schematic showing one example of an apparatus for using a continuous flow of $O_X$ to increase solubility and dispersibility in accordance with the method of the embodiment in FIG. 1.

Referring to FIG. 2, according to an embodiment of the invention, an apparatus according to the invention may include a chamber 1 equipped with a gasketed door 2 that can be opened to accommodate placement of material 3 within the chamber 1 and tightly closed and latched. The chamber 1 permits a vacuum tight seal during the process. The chamber 1 is connected via piping and appropriate control valves 4 to a vacuum pump 5 and separately to a generator of $O_X$ 6, which, in turn is connected to a gas washer 14 and an air preparation regulated feed gas supply 15. The chamber 1 is jacketed by coils of metal tubing 11 through which heated or chilled water generated by a temperature control (e.g., glycol) system 7 may be pumped to regulate the temperature within the chamber 1 during the process. The entire process may be controlled and monitored by a programmable industrial process controller 8. The chamber 1 is also connected to a water vapor source 12 to provide humidity control.

According to the method of the embodiment, material 3 for which solubility and dispersibility are to be increased is placed within the chamber 1 and the door 2 is closed and latched. The process is then initiated by activating the process controller 8, which has previously been programmed with the appropriate process parameters such as pressure, temperature and humidity. The controller 8 first activates the vacuum pump 5 and ancillary valves 4 to reduce the chamber pressure to a preset level between, e.g., 0 and 20 lbs./in² depending on the pressure sensitivity of the product being treated, to introduce via the water vapor source 12 the desired humidity, and to maintain a desired temperature via the temperature control system 7. After the appropriate vacuum level has been reached, the controller 8 initiates treatment by activating the $O_X$ generator 6 and opening a control valve 10, allowing the washed $O_X$ stream to be drawn into, through and out of the chamber 1 by the pressure differential. The vacuum pump 5 and $O_X$ generator 6 operate continuously during the process.

Exposure to the $O_X$ gas mixture may be varied in time from several minutes to several hours, depending on the material being treated. Once the treatment phase is complete, the vacuum pump 5 and $O_X$ generator 6 are inactivated and fresh air is allowed to enter the chamber 1 via the air purge valve 13. All $O_X$ gases may then be passed through a commercially available catalytic destruct unit 9 which eliminates any residual $O_3$ and $O_1$. before the gas stream is discharged to the atmosphere. The treated material 3 can then be removed from the chamber 1 and is ready for use following appropriate tests to confirm increased solubility and dispersibility.

The present invention relates to processes for increasing the solubility and dispersibility of low moisture content materials by utilizing $O_X$. The moisture content of the material is not greatly changed during treatment.

The low moisture materials which may be treated bye present processes include any materials which are in need of increased solubility and dispersibility and which are capable of being contacted with $O_X$. Preferred are materials that are not readily soluble in water, especially psyllium. Such materials are readily chosen by one skilled in the art.

Psyllium comes from psyllium seed from plants of the Plantago genus. Various species such as *Plantago lanceolate, P. rugelii*, and *P. major* are known. Commercial psyllium includes the French (black; *Plantago indica*), Spanish (*P. psyllium*) and Indian (blond; *P. ovata*). Indian (blond) psyllium is preferred for use herein.

The present invention also relates to the psyllium that has been treated by the method described hereinbefore. Such psyllium fiber has improved purity and/or aesthetics versus psyllium treated by art known methods (such as by treatment with ethylene oxide; by extrusion as described, for example, in European Patent Application No. 105,195; and by aqueous isopropanol/hydrogen peroxide sanitization as described, for example, in U.S. Pat. No. 3,992,147, to Christian et al., the disclosures being incorporated herein by reference in their entirety), and may be processed such that it retains a substantially intact cell structure.

The present invention thus includes highly soluble and dispersible psyllium fiber having intact cell structure.

The present invention will be further illustrated by the following non-limiting example.

EXAMPLE

$O_x$ Treatment of Psyllium Husk (1) Parameters

Psyllium husk was treated with $O_X$ in accordance with the method of the invention. The following parameters were used during treatment.

| | |
|---|---|
| Treatment Time: | 20 hours |
| Relative Humidity: | 20% |
| Chamber Temperature: | 48° F. |
| Absolute Pressure in Chamber: | 5.7 PSIA |
| Ozone Concentration (at generator): | 5.85% |
| Ozone Generation Rate: | 62 pounds/24 hours |
| Gas Mixture: | 97% oxygen, 3% nitrogen |

The above data represents the process used to treat all of the psyllium samples. The variables above may be changed in accordance with the invention. For example, the gas mixture may be modified to contain up to 80% carbon dioxide.

Results

Figure 4:
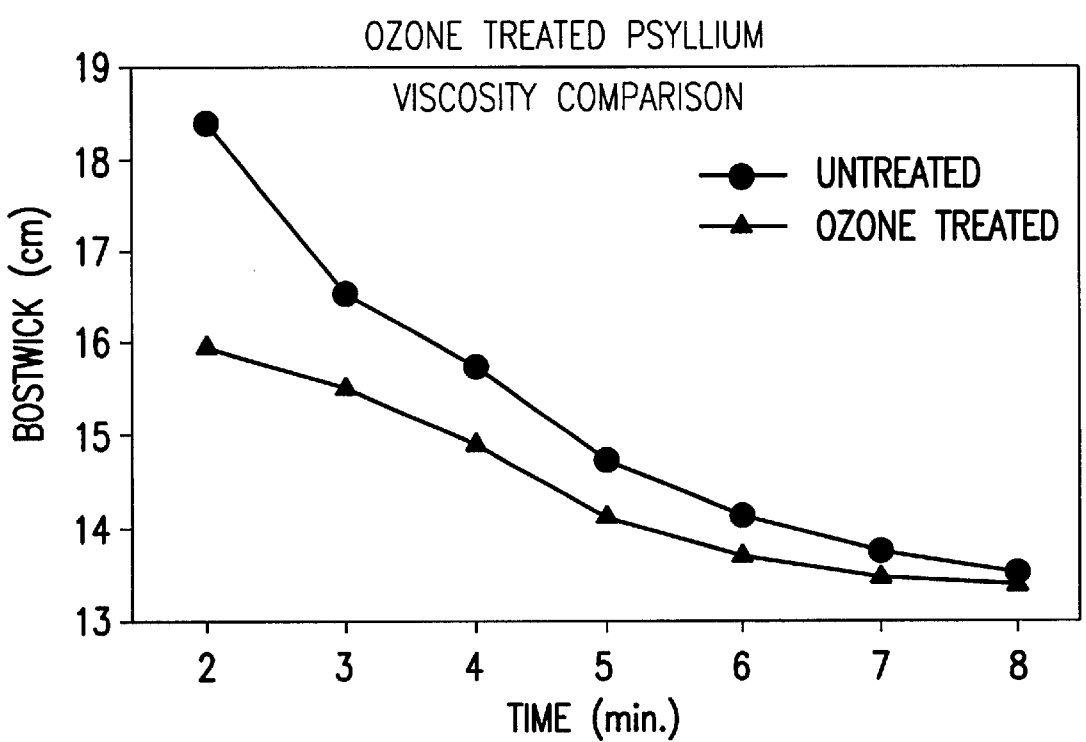
FIG. 4 is a graph comparing the viscosity of untreated and $O_X$ treated psyllium.

Standard psyllium/water solutions (5.4 g psyllium dissolved in 250 ml water @ 20° C.) were prepared and a Bostwick Consistometer was used to measure the flow of the untreated and the treated psyllium down an angled, walled ramp. The results of the measurements are shown below (see also FIG. 4):

| Time (minutes) | Bostwick (cm) (untreated) | Bostwick (cm) (treated) |
|---|---|---|
| 2 | 18.4 | 16 |
| 3 | 16.6 | 15.6 |
| 4 | 15.8 | 15 |
| 5 | 14.8 | 14.2 |
| 6 | 14.2 | 13.8 |
| 7 | 13.8 | 13.6 |
| 8 | 13.6 | 13.5 |

Viscosity is indicative of the solubility, or "wetability", of a substance. If a substance does not "wet", water will not assist dissolution and the gum system will not be able to hydrate resulting in a low viscosity solution. Thus, a lower viscosity is indicative of a lower solubility and a higher viscosity is indicative of a higher solubility.

The results above demonstrate a measurable increase in the gelling ability of the treated psyllium. A 10 to 15% increase in gelling strength has been observed. In addition to this observation, it was also noted that the $O_X$ treated material remained in suspension, wherein the untreated material settled out over time. A normal solution of untreated psyllium (5.4 g psyllium dissolved in 250 ml water @ 20° C.) will settle out of suspension within 1 to 3 minutes.

While it is desirable to prepare the psyllium according to the present invention such that the product completed is ready for ingestion by mixing it in a liquid, it is also possible to add additional materials (e.g., sweetening agents; flavoring agents; coloring agents; pharmaceutical agents; and mixtures thereof) to the agglomerated psyllium husk to provide the psyllium-containing drink mix product. Typically these additional materials (e.g., in amounts from about 0.01% to about 75%) would be added by dry blending or mixing with the psyllium (e.g., from about 25% to about 99.99%), but any method which does not substantially adversely affect the mixability of the psyllium may be used.

It is apparent that the results demonstrated above apply to other commercial products that, like psyllium, (1) form a gelatinous mass on contact with water and (2) exhibit poor dispersibility and mixability in water. Like psyllium, hydration of such products takes place over the surface of agglomerated aggregates to form gel-coated lumps, the interiors of which are still substantially dry. These lumps are extremely difficult to disperse.

Thus, various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for increasing solubility of a material comprising a step of applying a continuous stream of $O_X$ to said material in a sealed chamber, wherein said $O_X$ includes oxygen and its radicals, wherein said $O_X$ is selected from an integer from 1 to 3, wherein a pressure within said sealed chamber is maintained between 2.91 psia and 14.5 psia, and wherein said $O_X$ is maintained at a concentration sufficient to increase a solubility of said material above a solubility of untreated material when said material is contacted with water.

2. The method of claim 1, further comprising continuously withdrawing $O_X$ from said sealed chamber.

3. The method of claim 1, further comprising creating a pressure differential within said chamber and maintaining said pressure differential while continuously applying said stream of $O_X$ to said material.

4. The method of claim 3, further comprising agitating said $O_X$ in said chamber to increase permeation of said $O_X$ into said material.

5. The method of claim 4, wherein forced air is used to agitate said $O_X$.

6. The method of claim 4, wherein said agitating distributes said $O_X$ evenly throughout said chamber.

7. The method of claim 4, further comprising:

(a) creating a vacuum within said chamber;

(b) generating $O_X$ in an $O_X$ generation cell;

(c) withdrawing a stream of $O_X$ from said $O_X$ generation cell into said chamber; and (d) withdrawing $O_X$ from said chamber.

8. The method of claim 7, wherein said $O_X$ in said chamber is maintained at a concentration of about 0.1% to about 100% per total volume of gases in said chamber.

9. The method of claim 8, wherein $O_3$ in said chamber is maintained at a concentration of about 0.1% to about 25% per total weight of gases in said chamber.

10. The method of claim 9, wherein said $O_3$ in said chamber is maintained at a concentration of about 3% to about 16% per total weight of gases in said chamber, wherein an amount of $O_3$ used is dependent on said material.

11. The method of claim 3, wherein said $O_X$ generation cell comprises an $O_X$ generator capable of generating $O_X$ at a pressure of less than 20 lbs/in$^2$ selected from one or more of the group consisting of corona discharge, high frequency electrical discharge, ultraviolet light, x-ray, radioactive isotopes and electron beam.

12. The method of claim 7, further comprising maintaining a pressure differential between a pressure within said $O_X$ generation chamber and a pressure within said chamber sufficient to continuously withdraw said $O_X$ through said chamber.

13. The method of claim 12, further comprising controlling water vapor present in said continuous stream of $O_X$, prior to applying said continuous stream of $O_X$ to said material.

14. The method of claim 1, further comprising applying a continuous stream of one or more of a gas selected from the group consisting of $N_2$, $CO_2$ and Ar in addition to said continuous stream of $O_X$.

15. The method of claim 1, wherein said material is a dietary supplement comprising:

a material that is not naturally soluble in water.

16. The method of claim 15, wherein said dietary supplement comprises psyllium.

17. An apparatus for increasing solubility of a material, comprising:

(a) a chamber;

(b) a vacuum pump coupled to said chamber;

(c) an $O_X$ generation cell, wherein said $O_X$ generation cell comprises a means for generating $O_X$;

(d) a first control valve coupled to said chamber and said $O_X$ generation cell, wherein said first control valve is capable of permitting said $O_X$ to be withdrawn from said $O_X$ generation cell into said chamber; and (e) a second control valve coupled to said chamber, wherein said second control valve is capable of withdrawing $O_X$ contained within said chamber.

18. The apparatus of claim 17, further comprising a member for creating forced air contained within said chamber, wherein said forced air distributes said $O_X$ evenly throughout said chamber.

19. The apparatus of claim 17, further comprising a temperature-regulating means.

20. The apparatus of claim 17, further comprising a means for controlling water vapor coupled to said chamber.

21. The apparatus of claim 17, further comprising a controller for controlling and monitoring physical parameters within said chamber.

* * * * *